(12) United States Patent
Villemejane et al.

(10) Patent No.: US 8,705,223 B2
(45) Date of Patent: Apr. 22, 2014

(54) METHOD FOR PRODUCING INSULATED ELECTRODES FOR APPLYING ELECTRIC FIELDS INTO CONDUCTIVE MATERIAL

(75) Inventors: Julien Villemejane, Massy (FR); Bruno Le Pioufle, Paris (FR); Luis Maria Mir, Verrieres le Buisson (FR); Olivier Francais, Melun (FR); Jean-Pierre Lefevre, Puteaux (FR)

(73) Assignees: Centre National de la Recherche Scientifique (CNRS), Paris (FR); Ecole Normale Superieure de Cachan, Cachan (FR); Institut Gustave-Roussy, Villejuif (FR)

( * ) Notice: Subject to any disclaimer, the term of this patent is extended or adjusted under 35 U.S.C. 154(b) by 332 days.

(21) Appl. No.: 13/059,165

(22) PCT Filed: Aug. 20, 2009

(86) PCT No.: PCT/EP2009/060787
§ 371 (c)(1),
(2), (4) Date: Feb. 15, 2011

(87) PCT Pub. No.: WO2010/020674
PCT Pub. Date: Feb. 25, 2010

(65) Prior Publication Data
US 2011/0141649 A1   Jun. 16, 2011

(30) Foreign Application Priority Data
Aug. 20, 2008   (EP) ..................... 08162701

(51) Int. Cl.
*H05F 3/00*  (2006.01)
*B29C 33/40*  (2006.01)
*B29C 67/00*  (2006.01)

(52) U.S. Cl.
USPC ................ 361/225; 315/58; 249/83; 264/225

(58) Field of Classification Search
USPC ................ 361/225; 315/58; 249/83; 264/225
See application file for complete search history.

(56) References Cited

U.S. PATENT DOCUMENTS 4,213,238 A * 7/1980 Gudorf ........................... 29/878
5,674,267 A 10/1997 Mir et al.
(Continued)

FOREIGN PATENT DOCUMENTS

WO   WO 98/43702   10/1998
WO   WO 99/01158    1/1999
(Continued)

OTHER PUBLICATIONS

Coster, H. G. L.; A Quantitative Analysis of the Voltage-Current Relationships of Fixed Charge Membranes and the Associated Property of "'Punch-Through;'" Biophysical Journal, vol. 5, 1965; pp. 669-686.

(Continued)

*Primary Examiner* — Rexford Barnie
*Assistant Examiner* — Zeev V Kitov
(74) *Attorney, Agent, or Firm* — Harness, Dickey & Pierce, P.L.C.

(57) ABSTRACT

The present disclosure relates to a method for producing an insulated electrode comprising a conductive material coated with an electrically insulating material. The method includes at least the following steps of:
  forming a mold in an electrically insulating material, the mold including at least one channel, the mold being adapted to confine a conductive material,
  introducing the conductive material in a liquid state into the channel of the mold, the conductive material having a melting point that is lower than the melting point of the electrically insulating material.

8 Claims, 6 Drawing Sheets

(56) References Cited

U.S. PATENT DOCUMENTS

| | | | |
|---|---|---|---|
| 5,925,069 | A | 7/1999 | Graves et al. |
| 6,208,892 | B1 | 3/2001 | Agee |
| 6,261,831 | B1 | 7/2001 | Agee |
| 6,337,443 | B1 * | 1/2002 | Dlugas et al. ............. 174/120 R |
| 6,355,401 | B1 | 3/2002 | Graves et al. |
| 6,488,538 | B1 * | 12/2002 | Matsuba et al. ............. 439/615 |
| 6,734,633 | B2 * | 5/2004 | Matsuba et al. ................ 315/58 |
| 6,862,805 | B1 * | 3/2005 | Kuzma et al. ................... 29/858 |
| 6,977,172 | B2 | 12/2005 | Burke et al. |
| 7,742,809 | B2 | 6/2010 | Sigg et al. |
| 8,058,043 | B2 * | 11/2011 | Raffa et al. ................ 435/173.7 |
| 2004/0238484 | A1 | 12/2004 | Le Pioufle et al. |
| 2005/0040044 | A1 | 2/2005 | Frenea et al. |
| 2007/0043397 | A1 | 2/2007 | Ocel et al. |
| 2007/0198066 | A1 | 8/2007 | Greenberg et al. |
| 2008/0045826 | A1 | 2/2008 | Greenberg et al. |
| 2008/0063866 | A1 | 3/2008 | Allen et al. |
| 2008/0260588 | A1 | 10/2008 | Griscom et al. |
| 2010/0035322 | A1 | 2/2010 | Raffa et al. |

FOREIGN PATENT DOCUMENTS

| | | |
|---|---|---|
| WO | WO 99/24082 | 5/1999 |
| WO | WO 2008/062378 | 5/2008 |
| WO | WO 2010/010085 | 1/2010 |

OTHER PUBLICATIONS

Vernier, P. T. et al.; "Nanoelectropulse-Driven Membrane Perturbation and Small Molecule Permeabilization;" BMC Cell Biology, vol. 7, No. 37, 2006; pp. 1-16.

Mir, L. M. et al.; "Standard Operating Procedures of the Electrochemotherapy: Instructions for the Use of Bleomycin or Cisplatin Adminstered Either Systemically or Locally and Electric Pulses Delivered by the Cliniporator™ By Means of Invasive or Non-Invasive Electrodes;" Eur. J. of Cancer Supplements, special issue "Electrochemotherapy" 4, 2006; pp. 14-25.

Neumann, E. et al.; "Permeability Changes Induced by Electric Impulses in Vesicular Membranes;" J. Membrane Biol. 10, 1972; pp. 279-290.

Mir, L. M. et al.; "High-Efficiency Gene Transfer Into Skeletal Muscle Mediated by Electric Pulses;" Proc. Natl. Acad. Sci USA, 96, 1999; pp. 4262-4267.

Marty, M. et al.; "Electrochemotherapy—An Easy, Highly Effective and Safe Treatment of Cutaneous and Subcutaneous Metastases: Results of ESOPE (European Standard Operating Procedures of Electrochemotherapy) Study;" Eur. J. of Cancer Supplements, special issue "Electrochemotherapy" 4, 2006; pp. 3-13.

Belehradek Jr., J. et al.; "Electropermeabilization of Cells in Tissues Assessed by the Qualitative and Quantitative Electroloading of Bleomycin;" Biochimica et Biophysica Acta 1190, 1994; pp. 155-163.

Jaroszeski, M. J. et al.; "Delivery of Genes In Vivo Using Pulsed Electric Fields;" Methods in Molecular Medicine, vol. 37: Electrically Mediated Delivery of Molecules to Cells, 2000; pp. 173-186.

Zimmerman, U. et al.; "Dielectric Breakdown of Cell Membranes," Biophysical Journal, vol. 14, 1974; pp. 881-899.

Crowley, J. M.; "Electrical Breakdown of Bimolecular Lipid Membranes as an Electromechanical Instability;" Biophysical Journal, vol. 13, 1973; pp. 711-724.

White, J. A. et al.; "Stimulation of Capacitative Calcium Entry in HL-60 Cells by Nanosecond Pulsed Electric Fields;" The Journal of Biological Chemistry, vol. 279, No. 22, 2004; pp. 22964-22972.

Vernier, P. T. et al.; "Calcium Bursts Induced by Nanosecond Electric Pulses;" Biochemical and Biophysical Research Communications 310, 2003; pp. 286-295.

Stacey, M. et al.; "Differential Effects in Cells Exposed to Ultra-Short, High Intensity Electric Fields: Cell Survival, DNA Damage, and Cell Cycle Analysis;" Mutation Research 542, 2003; pp. 65-75.

Chen, N. et al.; "Leukemic Cell Intracellular Responses to Nanosecond Electric Fields;" Biochemical and Biophysical Research Communications 317, 2004; pp. 421-427.

Beebe, S. J. et al.; "Diverse Effects of Nanosecond Pulsed Electric Fields on Cells and Tissues;" DNA Cell Biology, vol. 22, No. 12, 2003; pp. 785-796.

Schoenbach, K. H. et al.; "Intracellular Effect of Ultrashort Electrical Pulses;" Bioelectromagnetics 22, 2001; pp. 440-448.

Neumann, E. et al.; "Gene Transfer Into Mouse Lyoma Cells by Electroporation in High Electric Fields;" The EMBO Journal, vol. 1, No. 7, 1982; pp. 841-845.

Beebe, S. J. et al.; "Nanosecond, High-Intensity Pulsed Electric Fields Induce Apoptosis in Human Cells;" The FASEB Journal, vol. 17, Aug. 2003; pp. 1493-1495.

Hall, E.H. et al.; "Nanosecond Pulsed Electric Fields (nsPEF) Induce Direct Electric Field Effects and Biological Effects on Human Colon Carcinoma Cells"; DNA Cell Biology, vol. 24, No. 5, 2005; pp. 283-291.

Chun-Guang, Wang et al.; "In Vivo Anti-Tumor Effect of siRNA Against STAT3 on Transplanted Lewis Lung Cancer in Mice;" Chemical Research in Chinese Universities, Beijing, CN, vol. 24, No. 3, XP025465993, May 1, 2008; pp. 330-337.

Villemejane, J.; "These De Doctorat De L'Ecole Normale Superieure De Cachan"; tel-00540353, version 1; Nov. 26, 2010; pp. 1-18 (Preface and Table of Contents); pp. 1-109, pp. 120-121, pp. 123-160, pp. 165-210, pp. xlvii-xlix, Illustration, 1 page, "Resume", 1 page.

Villemejane, J.; "Insulated Liquid Electrodes in a Microfluidic Chip for the Electroporation of Living Cells"; Proceedings of the 1$^{st}$ European Conference on Microfluidics—Microfluidics 2008—Bologna, Italy, Dec. 10-12, 2008; pp. 1-10.

Villemejane, J.; "Nanomanipulation of living cells on a chip using electric field"; tel-00540353, version 1; Nov. 26, 2010; 4 pages.

Villemejane, J., et al.; "Revue: Physical methods of nucleic acid transfer: general concepts and applications"; British Journal of Pharmacology; 2009; p. iii.

Mottet, G., et al.; "Article: A technique to design complex 3D lab on a chip involving multilayered fluidics, embedded thick electrodes and hard packaging—application to dielectrophoresis and electroporation of cells"; Journal of Micromechanics and Microengineering; 2010; p. xxxvii, pp. 1-8.

Silve, A., et al.; "Nanosecond Pulsed Electric Field Delivery to Biological Samples: Difficulties and Potential Solutions"; Advanced Electroporation Techniques in Biology and Medicine / CRC Press—M. Markov; Chapter 18, 2010; p. xix; pp. 1-16.

Villemejane, J. et al.; "Themed Section: Vector Design and Drug Delivery—Review—Physical methods of nucleic acid transfer: general concepts and applications"; British Journal of Pharmacology; 2009; pp. 207-219.

Kim, J.H. et al.; "High Throughput and High Efficiency Electroporation Chip With Polyelectrolyte Current Paths"; Eleventh International Conference on Miniaturized Systems for Chemistry and Life Sciences; Oct. 7-11, 2007, Paris, France; pp. 1339-1341.

Valero, A. et al.; "Gene transfer and protein dynamics in stem cells using single cell electroporation in a microfluidic device"; Lab on a Chip—Miniaturisation for chemistry, biology & bioengineering; vol. 8, No. 1, Jan. 2008; pp. 62-67.

* cited by examiner

DC-3F, 45 min, 20 np, 45 kV/cm

LPB, S-MEN, 60 min, 20 np, 30 kV/6mm

METHOD FOR PRODUCING INSULATED ELECTRODES FOR APPLYING ELECTRIC FIELDS INTO CONDUCTIVE MATERIAL

CROSS-REFERENCE TO RELATED APPLICATIONS

This application is a National Phase Entry of International Application No. PCT/EP2009/060787, filed on Aug. 20, 2009, which claims priority to European Patent Application Serial No. 08162701.0, filed on Aug. 20, 2008, both of which are incorporated by reference herein.

FIELD OF THE INVENTION

The present invention is related to a method to produce insulated electrodes able to deliver electric pulses onto any organic or inorganic conductive material and/or any biological material including cells or cells tissues in vivo, ex vivo or in vitro. These electric pulses may be useful for example for the electrically mediated transfer of nucleic acids (i.e. genes) into cells or cells tissues, including electroporation and/or for the electromanipulation, in general, of the cells including cells membrane.

BACKGROUND

Electrically mediated gene transfer, also termed DNA electrotransfer or electrogenetherapy, uses various single or multiple-electrode designs such as arrays of two or more electrodes that typically are designed as needle electrodes for insertion into a tissue, said electrode being connected to a pulse generator. The method has been shown to be effective to electrotransfer plasmid DNA to various tissues: muscles, liver, skin, tumors, mouse testis, etc. . . .

Mechanisms by which electric pulses mediate DNA transfer into target cells are not well understood. Nevertheless, there is a common agreement that for an improved DNA transfer into tissues, cells in that tissue must be permeabilized. For the years 1960-1970, in vitro studies showed that pulsed electric fields (PEF) delivery on living cells induce a reversible or irreversible breakdown of the cell membranes, called electropermeabilization. Such a permeabilization can be achieved using simple runs of short square wave electric pulses (in the range of 100 [mu]s). This kind of pulses has been widely used for the local delivery of non-permeant anti-cancer drugs (like bleomycin or cisplatin) in a treatment termed 'antitumor electrochemotherapy. Indeed, the delivery to tumors of e.g. 8 pulses of 1300 V/cm and 100 [mu]s either in vitro or in vivo is sufficient to induce transient rearrangements of the cell membrane that allow non-permeant anticancer molecules like bleomycin to enter the cell by diffusion and to fully exert their cytotoxic activity.

These short permeabilizing electric pulses have also been shown to increase the transfer of plasmid DNA into several tissues. However, another type of square-wave electric pulses was applied to muscles, tumors, liver and some other tissues, and was found to be more effective for DNA electrotransfer. These pulses usually are of lower voltage but much longer duration (in the range of tens of milliseconds). It is assumed that this type of pulses or combination of pulses (in the range of 100 μs to 100 ms and 25 to 1500 V/cm) mediate DNA transfer into the cells by inducing two distinct effects that include cell permeabilization (like the short pulses) and DNA electrophoretic migration during the delivery of the electric field. This technique, called gene electrotransfer is used to internalize DNA plasmids in cells without causing irreversible damages on plasma membranes. Efficient electrotransfer into cells has been described in WO-A-99/01158 and in WO-A-98/43702 notably.

A new kind of PEF, nanosecond pulsed electric fields (nsPEF) is actually under study. nsPEF are ultra-short pulses (10 ns, or even less than 10 ns to 300 ns) with higher electric field strength (10 to 150 kV/cm or more) that do not increase the temperature of the exposed cells. First studies showed that nsPEF induced permeabilization of intracellular membranes (granules, vesicles, mitochondria, nucleus . . . ) but not of plasma membrane.

nsPEF also have been shown to induce a release of intracellular calcium from the endoplasmic reticulum in cells under conditions maintaining plasma membrane integrity. Differential effects in cells exposed to ultra-short, high intensity electric fields have been studied by means of cell survival, DNA damage, and cell cycle analysis. nsPEF also have been shown to induce an enhancement of gene transfection efficiency. Within these studies, one experiment showed that the application of 1 nsPEF (10 ns, 150 kV/cm) 30 min after the GFP gene electrotransfer into cells in suspension allows an increase of 3-fold of the GFP expression compared to electrotransfer only. As the electrogenetransfer, like the other approaches for non viral gene therapy, is considered less efficient than the viral approaches for gene therapy, an increase of 3-fold or more of the GFP reporter gene expression is very important for the development of this non-viral gene therapy approach, which is considered, in general, safer and easier than the viral approaches.

Moreover, electroporation has been applied for delivering molecules to subsurface tissues using various single or multiple-electrode designs such as arrays of two or more electrodes that typically are designed as needle electrodes for insertion into said tissue, said electrode being connected to a pulse generator. Generally, such arrays define a treatment zone lying between the needle electrodes of the array. Such treatment zones therefore comprise a three dimensional volume of tissue wherein cells within the treatment zone are exposed to an electric field of an intensity sufficient to cause temporary or reversible poration, or even sometimes irreversible poration, of the cell membranes to those cells lying within and or near the three dimensional volume. The U.S. Pat. No. 5,674,267 discloses such a process and an electric pulse applicator for the treatment of biological tissue applying an electric field to the cells of biological tissue to modify the properties of their membranes.

Current practices for electroporating cells in tissue include use of significant voltages in order to impart through the three dimensional treatment zone a relatively uniform electric field. By "relatively uniform" is meant that electric lines of force coincident with application of an electric pulse sufficient to cause poration is imparted across the cells somewhat evenly throughout the three dimensional treatment zone volume. Besides the invasive aspect of a device with multiple needles, typical electroporation techniques, as stated above, result in variability in electroporation of cells within a treatment zone. This is a drawback to medical use of electroporation in that dispersion of treatment molecules of the injected bolus into surrounding tissue results in loss of control as to the amount of such treatment molecule that is ultimately transfected into cells within the treatment zone by the electroporation event.

Moreover, the use of metallic electrodes on contact of the skin or of the biological tissues may cause burns which are visible on the skin and which can be painful for a patient. These burns are probably of electrochemical kind. Indeed, the oxidizable metal of electrodes and the molecule of H2O and NaCl present in the surrounding of electrodes and on contact of said electrodes create various reactive species when the pulses are delivered. To avoid, or to reduce these burns, it is necessary to use biocompatible materials, for example specific metals or alloys, to elaborate the electrodes. This constraint may preclude the use of materials with optimal electrical properties (conductivity, permittivity) that may contain heavy metals, toxic ions, or, in general, non biocompatible substances. The electrochemical burns may affect normal cells reducing the efficacy of the electrogenetransfer or reducing the volumes treated by electrochemotherapy (as the electric pulses by themselves does not kill the cells in this application, and the bleomycin is killing almost exclusively the malignant tumor cells and sparing the non-dividing normal cells). Moreover, the ultrashort nanopulses seem to be unable to provoke the contraction of the muscles located in the contact or close to the electrodes, which can add comfort to the patient with respect to the treatment by electrochemotherapy using classical 100 µs-long pulses.

To overcome these drawbacks, it has been already imagined using insulated electrodes to deliver electric pulses onto any organic or inorganic conductive material and/or any biological material and/or to cells in vivo, ex vivo or in vitro, for example for the electroporation of the cells, for the electrically mediated transfer gene transfer of nucleic acids into tissue cell using a pulsed electric field and/or for the electromanipulation, in general, of the cell membrane or of the cell inside. Such insulated electrodes are disclosed in the European patent application EP08290714.8 filed Jul. 21, 2008 by the applicant. Said electrode includes a conductive main body and an electrically insulating coating and is intended to be introduced into and/or at the vicinity of a conductive material to be treated, for an electric pulse applicator for the treatment of conductive material, said electric pulse applicator comprising a pulse generator sending pulses to the electrodes having a slope (dE/dt) greater than $10^{15}$ V/m/s. In these conditions of pulse, the electrically insulating coating of electrodes looses its insulating properties allowing the generation of a "nanopulsed" electrical field.

The electrodes are usually rigid and machined with a cutting tool or molded before coating in such a manner that the shapes and the dimensional accuracy are limited, more particularly for electrodes of small dimensions. Consequently, there is a need in one hand for a method for producing rigid or flexible insulated electrodes with any desired shape, including 3D shape, and dimensions, including small dimensions, and on the other hand for a device allowing the real time observation of the effect of high electric field on material biological.

SUMMARY

The above-mentioned needs are addressed by the embodiments described herein in the following description. In one embodiment, a method for producing an insulated electrode comprising a conductive material coated with an electrically insulating material is provided. Said method comprises at least the following step of:
  forming a mould in an electrically insulating material, said mould comprising at least one channel, said mould being adapted to confine a conductive material
  introducing the conductive material in a liquid state into the channel of said mould, said conductive material having a melting point that is lower than the melting point of the electrically insulating material.

The conductive material is in a solid or malleable or liquid state at room temperature. 'Malleable' means according to the invention a material susceptible to change its form under the action of an external force and able to preserve its new form when the force does not act any more. It means particularly a material with plastic properties which is easily workable.

Moreover, the insulating material is selected among the group consisting of an inorganic insulating material, an organic insulating material, and combinations thereof. The inorganic insulating material is selected among glass, and mineral oxides, or nitrides. The organic insulating material is selected among elastomer, polymer materials, cellulose materials and lipidic materials.

The mould is advantageously formed by at least the following step:
  forming a photosensitive layer onto a support substrate,
  patterning the photosensitive layer,
  pouring a first layer of electrically insulating material onto the substrate in such a manner to obtain an intermediate substrate comprising a support substrate with a layer including the insulating material patterned by the photosensitive material,
  possibly and advantageously a second layer of insulating material can be bonded onto the intermediate substrate,
  removing the support substrate and the pattern of photosensitive material,
  bonding a third layer of insulating material layer onto the first molded insulated material including the pattern.

Patterning the photosensitive layer may be obtained by any method known in the art, including advantageously photolithography and micro-photolithography processes. In a particular embodiment, the pattern may be obtained by the following steps of:
  applying a mask on the photosensitive layer with the pattern of the mould,
  applying a UV illumination through photolithography process to the photosensitive layer through the mask,
  removing the mask and developing the photosensitive layer in order to obtain a pattern onto the substrate, Alternatively, the mould is formed by at least the following steps:
  forming at least one channel in at least one insulating layer,
  bonding a second insulating layer onto the first insulating layer.

The layers of insulating materials are the same or different.
  At least one of the layers of insulating material is a transparent insulating layer.

In one embodiment, at least one of the layers of insulating material is a rigid insulating layer. Preferably, the rigid electrically insulting layer is made with glass. The other insulating layer can be made in a rigid or flexible material, depending on the targeted application. In another embodiment, at least one of the layers of insulating material presents flexibility properties.

The present invention also concerns an insulated electrode comprising a conductive material coated with an electrically insulating material is provided. Said electrode comprises a malleable and conductive main body and an insulating coating. This insulating coating might be flexible or rigid, depending on the targeted application.

The method according to the invention is useful for the preparation of every dimensions of electrodes designed to be used either in vivo or in vitro. The method according to the invention is particularly useful for the preparation of small electrodes. These small electrodes have generally an height of about 5 to about 300 µm, preferably between about 50 and about 200 µm, more preferably around 100 µm. The other dimensions of the electrode can be comprised between about 10 µm and about 5 cm, possibly more, depending of the intended use of such electrode. The width of the insulating layers/coating is generally comprised between about 5 and 500 μm, preferably less than about 100 μm, more preferably about 10 μm and less than 50 μm. Insulated electrodes of the above dimensions are also part of the present invention and more particularly electrodes comprising a malleable and conductive main body as defined above.

In yet another embodiment, a device for the application of a pulsed electric field on a conductive material comprising an electric pulse applicator including at least two electrodes connected to a pulse generator sending pulses to the electrodes having a slope (dE/dt) greater than $10^{15}$ V/m/s is provided. Said device comprises at least two spaced electrodes including respectfully a main body and an electrically insulating layer lying between two rigid and transparent electrically insulating layers, the space between the electrodes forming a chamber wherein the conductive material to be treated can be introduced. Such insulated electrodes according to the present invention and/or obtained with the method according to the present invention are very useful for applications in optics, nonlinear optics, or spectroscopy, when electro-optical effects are initiated on chemical or biological molecules. More generally, they are useful in any application where the orientation of molecules on a transparent and/or flexible substrate is needed. Moreover, flexible insulating coating can also be useful for in vivo applications.

Electrodes according to the present invention and/or obtained with the method according to the present invention are also particularly useful with an electric pulse applicator and in the methods where an electric pulse is applied as described in EP 08290714.8 filed on 21 Jul. 2008, which content is incorporated herein by reference. Note that, without departing from the scope of the invention, the thickness of the electrically insulating layer can be greater, for specific industrial applications, or much lower.

BRIEF DESCRIPTION OF THE DRAWINGS

Embodiments of varying scope are described herein. In addition to the aspects described in this summary, further aspects will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical, chemical and other changes may be made without departing from the scope of the embodiments. The following detailed description is, therefore, not to be taken in a limiting sense.

Figure 1:
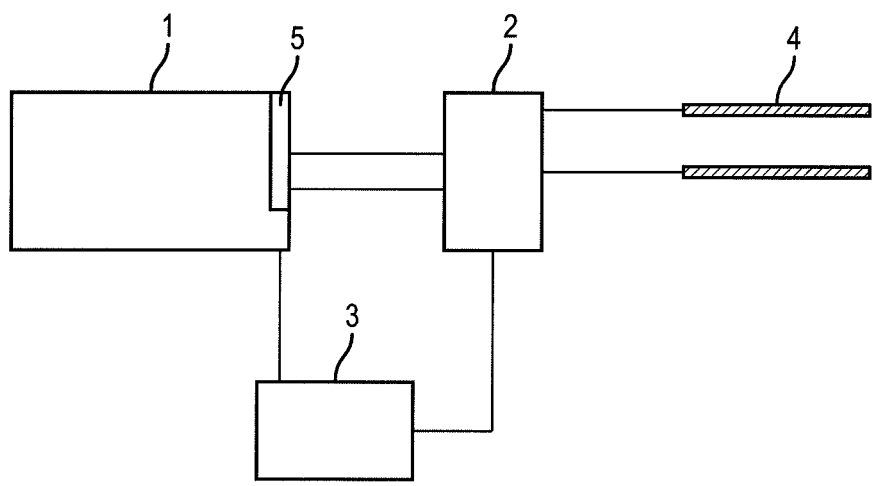
FIG. 1 illustrates a schematic representation of an electric pulse applicator according to the invention.

Referring to FIG. 1, the device for applying an electric field into biological material comprises a pulse generator 1, a selector switch 2, a control unit 3 and at least one electrode 4. Pulse generator 1 comprises a high voltage power supply 5 which is connected to the mains supply. The device according to the invention is intended to apply a variable electric field to cells and/or any biological material and/or any organic or inorganic conductive material located between a pair of electrodes 4, or close to one electrode 4 or to more than two electrodes 4.

Figure 2:
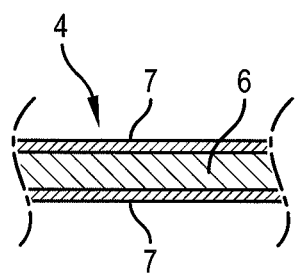
FIG. 2 illustrates a schematic representation of the section of a planar electrode of the electric pulse applicator according to the invention (or of a section of a no-planar electrode)

Each electrode 4 can be connected either to the positive or negative pole of the high voltage power supply 5. Moreover, referring to FIG. 2, each electrode includes a metallic main body 6, made in aluminium, copper, etc. . . . , or any conductive material, coated by an electrically insulating material 7. The whole of the electrode 4 is coated by the electrically insulating film, and the electric field that is generated in the biological object (cells, tissues, organs) or in any conductive non-biological object placed between the coated electrodes also pass through the insulating film. Of course in the present invention, the electrodes 4 can be completely coated, or they can be partially uncoated in the parts that are far from the biological or non biological object submitted to the electric pulses, or in the parts where two adjacent electrodes are the most apart, for example to facilitate the electrical connections with the pulse generator.

Said electrically insulating coating 7 can be an insulating inorganic, organic or mineral film such as a PDMS (Polydimethylsiloxane) film, an insulating glass, oxide, nitride, etc. . . . film, an insulating cellulose, lipidic, etc. . . . film, an insulating elastomer or polymer film, etc. . . . for example. The thickness of said insulating film can be about or less than 0.5 mm for example. Note that the thickness of the electrically insulating layer can be greater for specific industrial application without departing from the scope of the invention.

Control unit 12 controls the high tension power supply 13 and changeover switch 11 according to the instructions it receives from an operator or via a computer program. The device according to the invention is thus able to apply previously determined pulse cycles between electrodes 4. The pulses applied to each electrode 4 are rectangular-shape pulses, or trapezoidal, or triangular, or sinusoidal, or similar or have a shape which spectrum contains at least the spectrum of above mentioned signals, having an amplitude of about 100 V/cm to 200 kV/cm and a pulse length lower than 1 microsecond, and preferably comprised between 0.1 and 10 nanoseconds, and preferably of less than a nanosecond or a few nanoseconds, with a slope (dE/dt) of the raising front greater than $10^{15}$ V/m/s. In these conditions of pulse, the electrically insulating coating 7 of electrodes 4 looses its insulating properties allowing the generation of a "nanopulsed" electrical field.

It could be noted that the amplitude and the length of the pulse will be adapted by the operator in function of the use of the device and the kind of biological material: electrically mediated gene transfer of nucleic acids into tissue cell and/or electroporation and/or destruction of cells by irreversible electroporation, and/or any cell electromanipulation made feasible by the use of the nanopulses. The device according to the invention can notably be used for a tumor treatment by electrochemotherapy and/or electrotherapy and/or genetherapy. Moreover, the device according to the invention allows to free electrodes from biocompatibility constraints. In such a way, the main body of electrodes 4 can be obtained in any desired conductive material. This material can thus have different electrical properties (conductivity, permittivity) optimal for the tissue and for the desired procedure or treatment, without being limited to a choice among biocompatible authorized materials.

Figure 3:
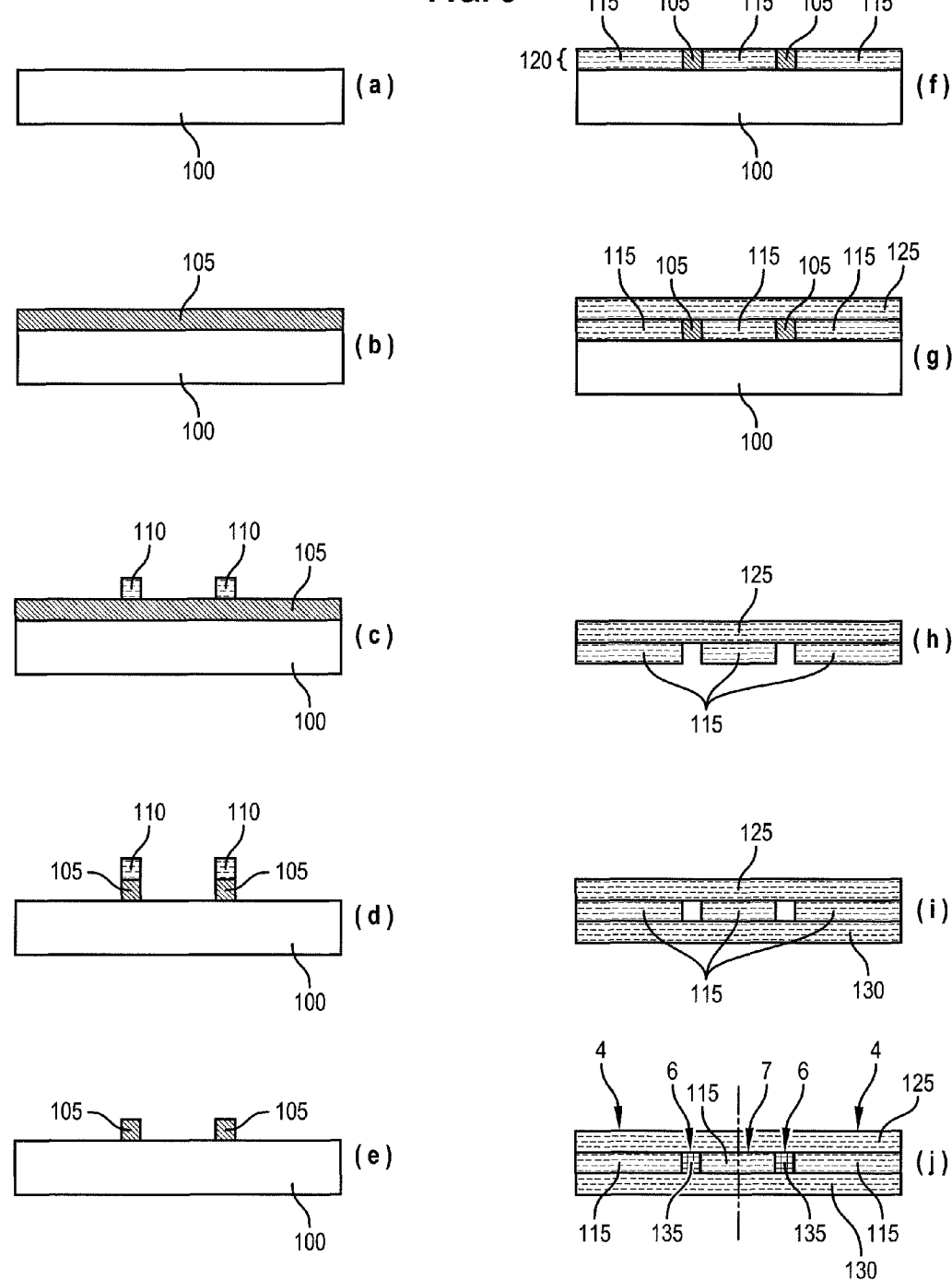
FIG. 3 illustrate a schematic representation of steps of the method for producing an electrode according to the invention.

Referring to FIG. 3, the method for producing an insulated electrode comprises a first step (FIG. 3*a*) of providing a support substrate 100 which can be obtained in silicium (Si) or in any convenient material, a second step (FIG. 3*b*) of forming a photosensitive layer 105 onto the support substrate 100. This photosensitive layer 105 can be obtained in SU-8 2075 (25 s at 1000 rpm) for example or in any appropriate material. SU-8 is marketed MicroChem® and consists of chemically amplified; epoxy based negative resists with high functionality, high optical transparency and are sensitive to near UV radiation. Cured films or topography are highly resistant to solvents, acids and bases and have excellent thermal stability.

Moreover, said photosensitive layer 105 is formed with a thickness comprised between 2 and 300 microns for example. It is understood that thicker layers can also be considered by the skilled person. Then a mask 110 is formed onto the photosensitive layer 105 (FIG. 3*c*) with the pattern of the desired mould to be obtained. Note that the pattern can have any desired shape in such a manner that the electrodes can have any desired shape including a 3D shape.

Following this step, a photolithography is applied (FIG. 3*d*) until the photosensitive layer 105 is removed and the mask 110 is removed (FIG. 3*e*) to obtain a pattern of photosensitive material onto the support substrate 100. Accessorily, the support substrate 100 and the pattern of photosensitive layer 105 is exposed to UV during about 45 s and baked 1 min at 65° C. and 12 min at 95° C. Then, it is developed in SU-8 developer during 15 min. This last step finishes by a hard bake at 180° C. during 30 min. Note that these steps will be easily adapted by the man skilled in the art depending of the material of the photosensitive layer 105.

Then, a first electrically insulating material 115 is poured (FIG. 3*f*) onto the substrate in such a manner to obtain an intermediate substrate comprising a support substrate 100 with a layer 120 including the insulating material 115 and the pattern of photosensitive material 105. This first electrically insulating material 115 is selected among the group consisting of an inorganic insulating material, an organic insulating material, and combinations thereof. Organic insulating material can consist in any synthetic material or material of natural origin. The organic insulating material is selected among elastomer, polymer materials, cellulose materials and lipidic materials notably. In this particular example, the first electrically insulating material 115 consists in Polydimethylsiloxane (PDMS) which is an insulating material having flexibility properties; nevertheless, said material can be substituted by any flexible or rigid insulating material without departing from the scope of the invention.

Then, referring to FIG. 3*g*, a second electrically insulating material layer 125 which consists in a glass plate of 1 mm of thickness is bonded onto the intermediate substrate. Note that the glass plate can be substituted by any rigid and transparent insulating layer without departing from the scope of the invention. In a next step, referring to FIG. 3*h*, the support substrate 100 and the pattern of photosensitive material 105 is removed.

Then, referring to FIG. 3*i*, a third electrically insulating material layer 130 which consists in a glass plate of 1 mm of thickness is bonded onto the opposite side of the intermediate substrate. Note that, in the same way, the glass plate can be substituted by any rigid and transparent insulating layer without departing from the scope of the invention.

Finally, referring to FIG. 3*j*, a conductive material 135 is introduced in a liquid state into the channel formed in the mould, said conductive material 135 having a melting temperature that is lower than the melting temperature of the electrically insulating material forming the mould. The conductive material will solidified and finally will be in a solid state at room temperature. Said conductive material can consists for example in a silver conductive resin; nevertheless, said conductive material can consist in any conductive material with a melting temperature lower than the melting temperature of the electrically insulating material forming the mould.

Figure 5:
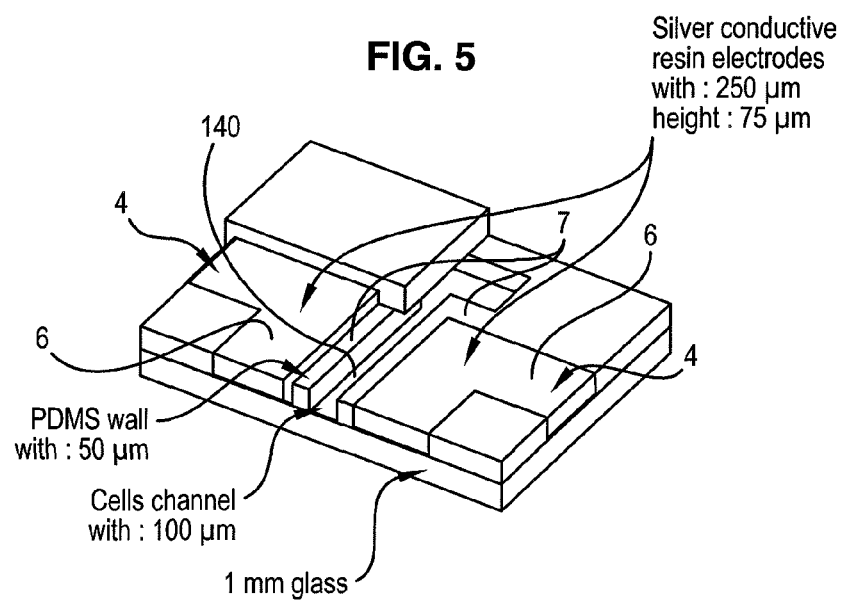
FIG. 5 is a perspective cutaway view illustrating a device for the application of a pulsed electric field on a conductive material comprising two insulated electrodes and a chamber wherein the conductive to be treated can be introduced.
Figure 6:
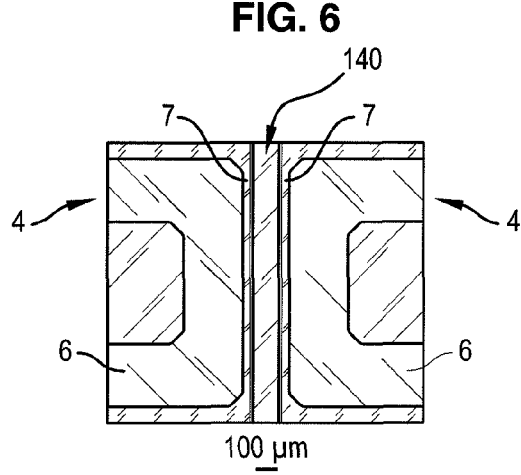
FIG. 6 is a partial top view of the device illustrated in FIG. 5.

The device thus obtained, referring to FIGS. 3*j*, 5 and 6, comprises two spaced electrodes 4, with a general U shape, including respectfully a main body 6 and an electrically insulating layer 7 lying between two rigid and transparent electrically insulating layers, the space between the electrodes forming a chamber 140 wherein the conductive material such as biological material to be treated can be introduced. Such a device is compatible to the real time observation under microscope of cells during electroporation because of the transparency and planarity of the device and because of the biocompatibility of materials in contact with cells. Note that the chamber 140 of said device looks like a channel with a constant width; nevertheless, the chamber 140 can be obtained with different widths along its longitudinal axis.

Figure 4:
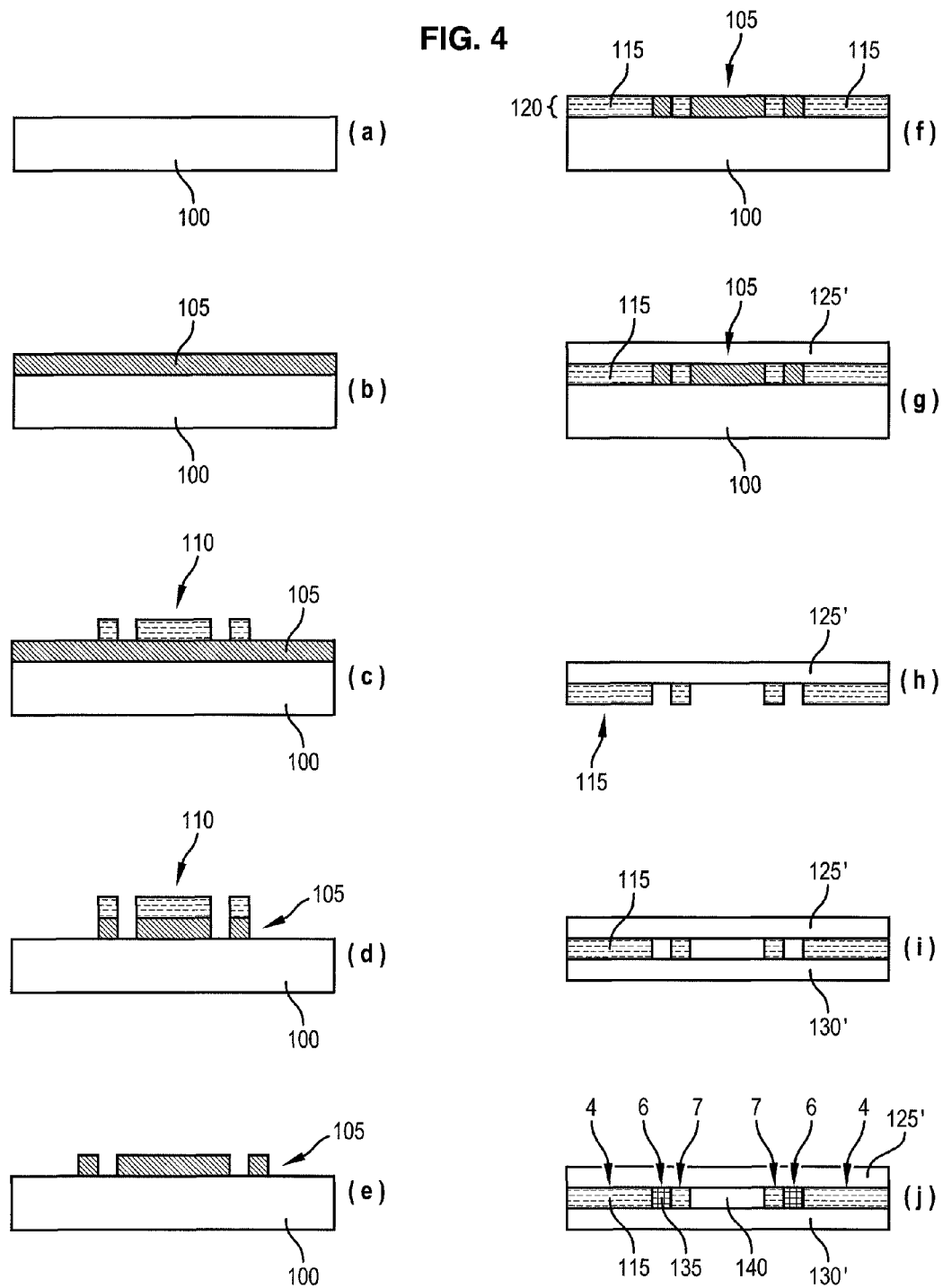
FIG. 4 illustrates a schematic representation of steps of the method for producing a device for the application of a pulsed electric field on a conductive material according to the invention.

In another embodiment, referring to FIG. 4, the method for producing an insulated electrode comprises, as above, a first step (FIG. 4*a*) of providing a support substrate 100 which can be obtained in silicium (Si) or in any convenient material, a second step (FIG. 4*b*) of forming a photosensitive layer 105 onto the support substrate 100. This photosensitive layer 105 can be obtained in SU-8 2075 (25 s at 1000 rpm) for example or in any appropriate material. Moreover, said photosensitive layer 105 is formed with a thickness comprised between 2 and 300 microns for example.

Then a mask 110 is formed onto the photosensitive layer 105 (FIG. 4*c*) with the pattern of the desired mould to be obtained. Note that the pattern can have any desired shape in such a manner that the electrodes can have any desired shape including a 3D shape. Following this step, a photolithography is applied (FIG. 4d) until the photosensitive layer 105 is removed and the mask 110 is removed (FIG. 4e) to obtain a pattern of photosensitive material onto the support substrate 100.

Accessorily, the support substrate 110 and the pattern of photosensitive layer 105 is exposed to UV during about 45 s and baked 1 min at 65° C. and 12 min at 95° C. Then, it is developed in SU-8 developer during 15 min. This last step finishes by a hard bake at 180° C. during 30 min. Note that these steps will be easily adapted by the man skilled in the art depending of the material of the photosensitive layer 105. Then, a first electrically insulating material 115 is poured (FIG. 4f) onto the substrate in such a manner to obtain an intermediate substrate comprising a support substrate 100 with a layer 120 including the insulating material 115 and the pattern of photosensitive material 105.

This first electrically insulating material 115 is selected among the group consisting of an inorganic insulating material, an organic insulating material, and combinations thereof. Organic insulating material can consist in any synthetic material or material of natural origin. The organic insulating material is selected among elastomer, polymer materials, cellulose materials and lipidic materials notably. In this particular example, the first electrically insulating material 115 consists in Polydimethylsiloxane (PDMS) which is an insulating material having flexibility properties.

Then, referring to FIG. 4g, a second electrically insulating material layer 125' which consists in a soft Polydimethylsiloxane (PDMS) layer is bonded onto the intermediate substrate. In a next step, referring to FIG. 4h, the support substrate 100 and the pattern of photosensitive material 105 is removed. Then, referring to FIG. 4i, a third electrically insulating material layer 130' which consists in a soft Polydimethylsiloxane (PDMS) layer is bonded onto the opposite side of the intermediate substrate. Note that, in the same way, second and the third electrically insulating material can be substituted by any insulating layer selected among the group consisting of an inorganic insulating material, an organic insulating material, and combinations thereof and having flexibility properties without departing from the scope of the invention.

Finally, referring to FIG. 4j, a conductive material is introduced in a liquid state into the channel formed in the mould, said conductive material having a melting temperature that is lower than the melting temperature of the electrically insulating material forming the mould. The conductive material will solidified and finally will be in a malleable state at room temperature.

Alternatively, the conductive material can remain in a liquid state at room temperature. The electrodes thus obtained include a malleable and conductive main body 6 and an electrically insulating coating 7 having flexibility properties. Accessorily, a plurality of electrodes can be obtained according to the aforementioned method and a cutting step can be applied to separate said electrodes.

In another embodiment, the mould can be obtained by forming at least one channel in at least one insulating layer by any conventional method such as mechanical or chemical etching or drilling for example, and bonding a second insulating layer onto the first insulating layer. For instance, in yet another embodiment, the second insulating material is made of poly(p-xylylene) polymer, such as parylene. One advantage of parylene is that it can be vapor deposited on the first insulating layer. This facilitates a homogeneous deposition of insulating coating on the first insulating layer. Preferentially, the second electrically insulating layer of parylene presents a thickness of less than 50 µm. This allows obtaining an insulated electrode having substantially the same dimensions as an electrode which is coated with a single insulating layer.

We will explain hereinafter the interest of the insulated electrodes obtain from the method according to the invention. Electrical properties of biological liquid are mostly defined by two variables: the conductance of the medium due to charges moving thanks to the electric field, and its polarisation which opposes to the applied field. The conductance is modelled by an electric resistance of expression:

$$R_{Bio} = \frac{e}{\sigma \cdot S}$$

where $\sigma$ is the conductivity, e the electrodes gap and S the average section of current flux in the medium. The polarization is described by an electric capacitance:

$$C_{Bio} = \varepsilon \cdot \frac{S}{e}$$

with $\varepsilon$ as absolute permittivity of the liquid.

Figure 7:
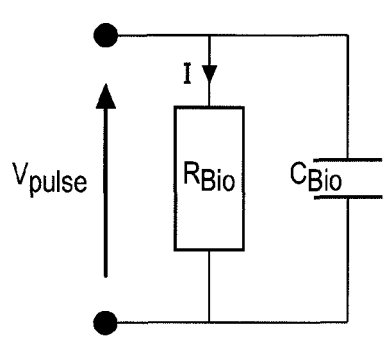
FIG. 7 is a schematic representation of an equivalent electric model of electroporation device with conventional electrodes, i.e electrodes without electrically insulated coating, in contact with the conductive material to be treated.

The electrical model of a biological fluid is thus described by those two elements $R_{Bio}$ and $C_{Bio}$ in parallel. When applying a voltage pulse to non isolated electrodes surrounding a biological liquid, a current $$I = \frac{U}{R_{Bio}}$$

appears while a charge $$Q = \frac{U}{C_{Bio}}$$

is stored in the liquid and discharged at the end of the pulse. This case corresponds to classical electroporation where the electrodes are directly in contact with the fluid (FIG. 7).

The electric time constant of the biological fluid is:

$$\tau_{Bio} = R_{Bio} \cdot C_{Bio} = \frac{\varepsilon}{\sigma}.$$

In our case, the conductivity (of a classical biological tissue or of an usual cell culture medium) is equal to 0.1 S/m and permittivity is equal to $80*8.8*10^{-12}$ F/m (close to water permittivity). So $\tau_{Bio}$=7 ns. It is obvious that other parameters could be considered.

Figure 8:
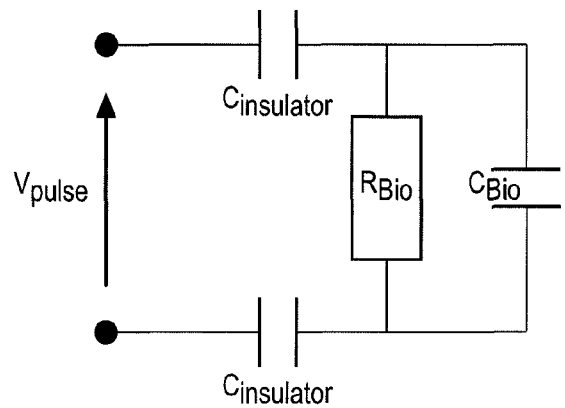
FIG. 8 is a schematic representation of an equivalent electric model of electroporation device with insulated electrodes according to the invention.
Figure 9:
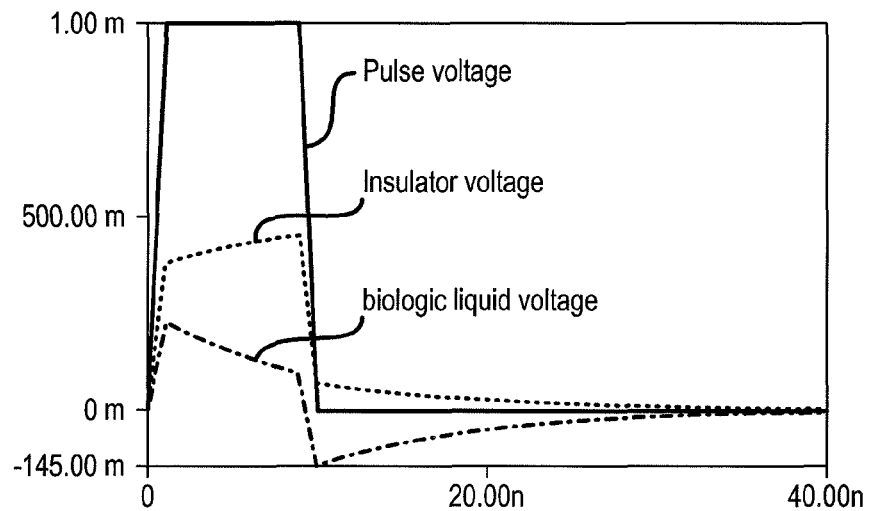
FIG. 9 is a graphical representation of the voltage evolution during a pulse of 10 ns.

When insulators are used to separate the electrodes from the biological liquid, two capacitances $C_{Insulator}$ (one for each insulator) have to be added in serial with the equivalent model (FIG. 8). The presence of these capacitances reduces the voltage applied on the biological liquid (FIG. 9), as the pulse amplitude is divided by the capacitor bridge. Moreover the current in the biological medium tends to zero even if the voltage is maintained. Indeed a voltage discharge is induced in the liquid with a time constant $\tau_{Bio}$. Using this configuration, the use of pulses longer than $\tau_{Bio}$, which is the case when microsecond pulses are applied, is meaningless. In other words the transfer function of the electric field in the biological fluid is a high pass filter which cut off frequency is $$\frac{1}{\tau_{Bio}}.$$

Figure 10:
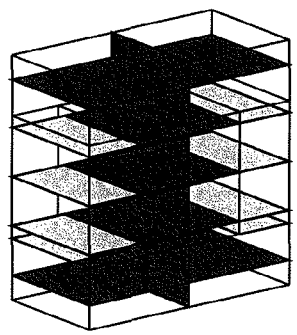
FIG. 10 is a graphical representation of the electric field distribution, high value in PDMS being compared to biological liquid.

In our case, where nanopulses (nsPEF) are applied (pulses which duration is less than 10 ns), this configuration involving insulated electrodes permits the application of consistant electrical field to the biological medium. An electric simulation (obtained with the software Simplorer® marketed by ANSOFT™) presented in FIG. 10, shows the effect of a voltage pulse of 10 ns (rising and falling time of 1 ns included). The parameters value, calculated from our device geometry, are: $C_{Insulator}=9$ nF, $C_{Bio}=14$ nF, $R_{Bio}=500$ Ω.

During rising and falling time of the pulse (1 ns each), the voltage on insulator and biological follow the pulse slope. During the pulse (8 ns), the electric discharge of the biologic liquid voltage leads to a decrease of the field. The simulation shows that only nanopulses can be transmitted to the biological liquid, as in the case of micropulses, the voltage will only be transmitted few nanoseconds. At the interface between insulator and biological medium, we can apply the Maxwell equations:

$$\text{div}\vec{D}=\text{div}(\epsilon.\vec{E})=0$$

and thus:

$$\epsilon_{rInsulator}.\epsilon_0.\vec{E}_{Insulator}.\vec{N}=\epsilon_{rBio}.\epsilon_0.\vec{E}_{Bio}.\vec{N}$$

As the field is normal to the surface of the insulator, we approximate:

$$\epsilon rInsulator.E_{Insulator}=\epsilon_{rBio}.E_{Bio}$$

So, the two electric fields are inversely proportional to their permittivity. Due to permittivity value $\epsilon_{rBio}=80$ and $\epsilon_{rInsulator}=2.8$, Electric field in insulator will be 28 higher than in the biological medium. It's a real limitation for electroporation with nanopulses where extremely high electric field (typically 45 kV/cm) are needed which might induce the PDMS dielectric breakdown. Investigations towards electric field reduction in insulator are underway.

Figure 11:
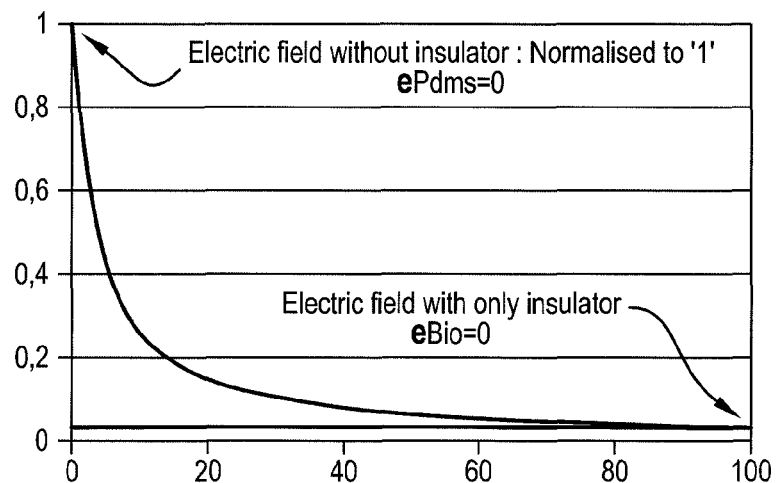
FIG. 11 is a graphical representation of the electric field evolution in biological liquid versus insulator thickness percentage.

Simulation of the electric field amplitude versus the insulator thickness had been done with the help of Comsol. Due to high aspect ratio of the electrode, electric field obtained in the liquid is homogenous (FIG. 10). It can be seen as a perfect capacitance without board effect. From simulation, illustrated in FIG. 11, the electric field value is extracted and normalized versus its value without insulator versus the insulator thickness. In FIG. 11, results are given with PDMS as insulator.

The insulator is rapidly decreasing the electric field value in the liquid. Here, 10% of insulator divides by 4 the field value in liquid. Simulations confirm the dependence of the two fields versus their own permittivity, ratio between the two fields is equal to ratio between permittivity.

DC-3F cells (Chinese hamster fibroblast lung cells) and LPB cells (mouse fibrosarcoma) were grown in the complete medium: Minimum Essential Medium (Invitrogen, Cergy-Pontoise, France) supplemented with 10% fetal bovine serum (Invitrogen), 500 U/ml penicillin, 500 μg/ml streptomycin (Invitrogen) defined as complete medium. Cultures were maintained in a humidified atmosphere with 5% CO2 at 37° C. Cells were routinely passed every two days. Plasmid pCMV-Luc (Clontech, Montigny-les-Bretonneux, France) was prepared using the Endotoxin-free Plasmid DNA (Macherey-Nagel, Hoerdt, France) according to manufacturer's protocol.

Cells were harvested by trypsin and cell suspension was placed into electroporation cuvettes in low conductivity medium (250 mM sucrose, 10 mM Tris, 1 mM $MgCl_2$, pH=7) ($10^6$ cells per electroporation cuvette). Cells were exposed to 8 electropermeabilizing pulses (1250 V/cm, 100 μs, 1 Hz) delivered by a Cliniporator (IGEA, Carpi, Italy) in the presence of DNA coding for the luciferase. After these pulses, cells were incubated for 45 to 60 min either at 37° C. under 5% $CO_2$.

Nanopulses were delivered by a high voltage generator FPG 10-30 MS (FID Technology—Russia). It can deliver electric pulses from 2.5 kV to 10 kV per output in an impedance of 1 kΩ and it has 4 similar outputs. Pulses last 10 ns and have transition time of 3 ns. An external trigger from TTY is used to set off the nsPEF generator.

Cells were exposed to nsPEF:
with contact between electrodes and the medium}: in electroporation cuvettes (Molecular BioProducts, VWR, France) which had a gap between the electrodes of 1 or 2 mm.
with insulated electrodes according to the invention: in spectroscopy cuvettes (Plastibrand, VWR, France) which had a gap between the electrodes of 6 mm and an insulating layer of 0.5 mm in PVC.

After the nsPEF delivery, cells were removed from the electroporation or spectroscopy cuvette and cultured in the complete medium for 24 hours at 37° C. under 5% $CO_2$.

Firstly, we investigated the fact that the use of insulated electrodes gave the same biological results than "conventional" electrodes on the enhancement of gene expression after an electrotransfer of plasmid DNA by using nanosecond pulsed electric field. It was shown by Beebe et al. (S. J. Beebe, J. White, P. F. Blackmore, Y. Deng, K. Somers, and K. H. Schoenbach. (2003). Diverse effects of nanosecond pulsed electric field on cells and tissues. DNA and Cell Biology, 22, 785) that the application of only 1 nsPEF (10 ns, 150 kV/cm) 30 min after the GFP gene electrotransfer into cells in suspension allows an increase of 3-fold of the GFP expression compared to electrotransfer. Here, the experiment consists in the electrotransfer of gene coding for the luciferase followed or not by the exposure to nsPEF (a) with conventional electroporation cuvettes (electrodes in contact with the medium) (20 nsPEF of 45 kV/cm, 45 min after the electrotransfer) and (b) with insulated electrodes (no contact between metal and liquid) (20 nsPEF of 30 kV, corresponding to a static electric field of 9 kV/cm in the medium, 60 min after the electrotransfer).

Figure 12:
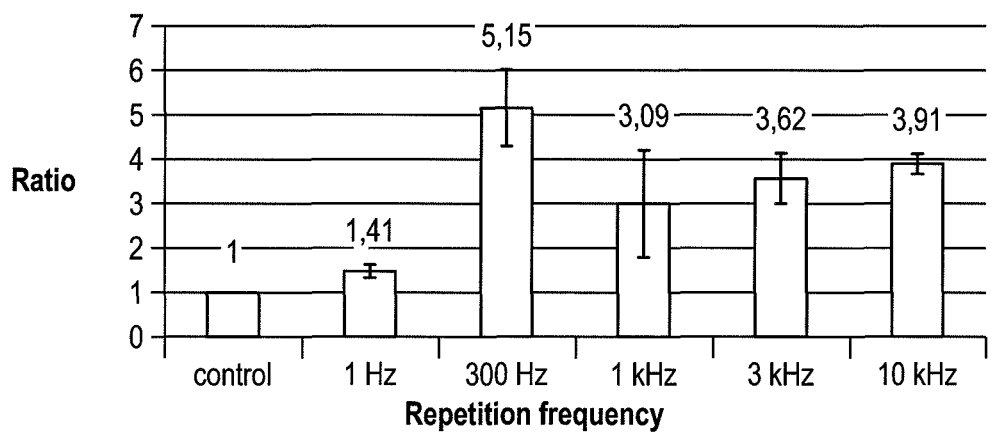
FIG. 12 illustrates the ratio of the luciferase activity between exposed cells to nsPEF after electrotransfer and electrotransfered cells depending on the repetition frequency of the pulses with cuvettes of electroporation of prior art.
Figure 13:
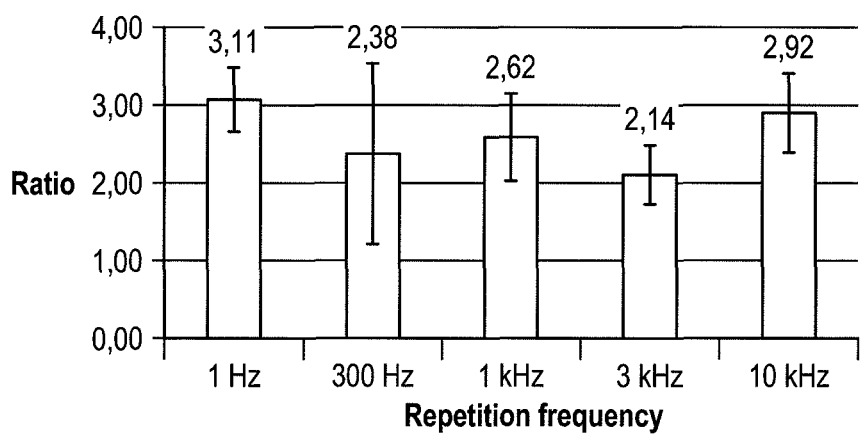
FIG. 13 illustrates the ratio of the luciferase activity between exposed cells to nsPEF after electrotransfer and electrotransfered cells depending on the repetition frequency of the pulses with insulated electrodes according to the invention.

FIGS. 12 and 13 show the ratio of the luciferase activity between exposed cells to nsPEF after electrotransfer and electrotransfered cells only (control) depending on the repetition frequency of the pulses. In both cases, with "conventional" cuvettes of electroporation (FIG. 12) and with insulated electrodes (FIG. 13), gene expression is enhanced by exposing cells to nsPEF 45 or 60 min after an electrotransfer of gene. In both cases, an increase of 3-fold of the gene expression can be reach, depending on several parameters (field intensity, repetition frequency . . . ). These results show the feasibility to use insulated electrodes to apply nsPEF on cells. The repetition frequency of the nsPEF appears to be less affecting the gene expression by using insulated electrodes.

The method for producing an insulated electrode allows the production of rigid or flexible insulated electrodes having:
any shape, including 3D shapes, as interlaced electrodes without interconnection,
any dimensions,
an homogeneity of the conductivity in the whole conductive material.

This written description uses examples to disclose the invention, including the best mode, and also to enable any person skilled in the art to make and use the invention. The scope of the subject matter described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for producing an insulated electrode, the method comprising:
   (a) forming a mold in an electrically insulating material, the mold comprising at least one channel, and the mold being adapted to confine a conductive material, the mold being formed by at least the following steps:
      forming a photosensitive layer onto a support substrate;
      patterning this photosensitive layer;
      pouring a first layer of the electrically insulating material onto the substrate to obtain an intermediate substrate comprising a support substrate with a layer including the insulating material and the pattern of photosensitive material;
      bonding a second layer of insulating material onto the intermediate substrate;
      removing the support substrate and the pattern of photosensitive material; and
      bonding a third layer of insulating material onto the first insulated material including the pattern; and
   (b) introducing the conductive material in a liquid state into the channel of the mold, the conductive material having a melting point that is lower than the melting point of the electrically insulating material;
   wherein the insulated electrode comprises the conductive material coated with the electrically insulating material.

2. The method according to claim 1, wherein the conductive material is in one of: a solid, malleable and liquid state at room temperature.

3. The method according to claim 1, wherein the insulating material is selected among the group consisting of an inorganic insulating material, an organic insulating material, and combinations thereof.

4. The method according to claim 3, wherein the inorganic insulating material is selected and consists of one of: glass, mineral oxides and nitrides.

5. The method according to claim 3, wherein the organic insulating material is selected and consists of one of elastomer, polymer materials, cellulose materials and lipidic materials.

6. The method according claim 1, wherein at least one of the layers of insulating material is a transparent insulating layer.

7. The method according to claim 1, wherein at least one of the layers of insulating material is a rigid insulating layer.

8. The method according to claim 7, wherein the rigid electrically insulting layer is made with glass.

* * * * *